US010597697B2

(12) United States Patent
Nelson et al.

(10) Patent No.: US 10,597,697 B2
(45) Date of Patent: Mar. 24, 2020

(54) METHOD OF DETERMINING A NUCLEOTIDE SEQUENCE OF A NUCLEIC ACID SEGMENT FROM A REGION OF INTEREST IN A BIOLOGICAL SAMPLE

(71) Applicant: GE Healthcare Bio-Sciences Corp., Marlborough, MA (US)

(72) Inventors: John Richard Nelson, Niskayuna, NY (US); Qingyan Au, Irvine, CA (US); Wei Gao, Niskayuna, NY (US); Ryan Charles Heller, Niskayuna, NY (US); Nicholas Hoe, Garden Grove, CA (US); Nam Tran, Aliso Viejo, CA (US); Nichole Lea Wood, Niskayuna, NY (US)

(73) Assignee: GE Healthcare Bio-Sciences Corp., Marlborough, MA (US)

( * ) Notice: Subject to any disclaimer, the term of this patent is extended or adjusted under 35 U.S.C. 154(b) by 718 days.

(21) Appl. No.: 15/003,450

(22) Filed: Jan. 21, 2016

(65) Prior Publication Data

US 2016/0230219 A1    Aug. 11, 2016

Related U.S. Application Data

(60) Provisional application No. 62/112,199, filed on Feb. 5, 2015.

(51) Int. Cl.
*G01N 33/53*    (2006.01)
*C12Q 1/6806*    (2018.01)
*G01N 33/58*    (2006.01)

(52) U.S. Cl.
CPC ......... *C12Q 1/6806* (2013.01); *G01N 33/582* (2013.01)

(58) Field of Classification Search
CPC ........................... C12Q 1/6806; G01N 33/582
See application file for complete search history.

(56) References Cited

U.S. PATENT DOCUMENTS

| 2005/0176068 A1* | 8/2005 | Emmert-Buck ... G01N 33/5091 435/7.2 |
| 2006/0046311 A1* | 3/2006 | Sun .................. G01N 33/54366 436/518 |
| 2006/0134692 A1* | 6/2006 | Emmert-Buck ..... G01N 33/543 435/7.1 |

(Continued)

OTHER PUBLICATIONS

Murphy et al., "Mate Pair Sequencing of Whole-Genome-Amplified DNA Following Laser Capture Microdissection of Prostate Cancer", DNA Research (Oct. 2012) 19(5):395-406 (Year: 2012).*

(Continued)

*Primary Examiner* — Christopher L Chin
(74) *Attorney, Agent, or Firm* — Eversheds Sutherland (US) LLP

(57) ABSTRACT

The invention discloses a method for determining a nucleotide sequence of a nucleic acid segment present in a biological sample, comprising the steps of: a) generating a fluorescent image of the sample by a protocol comprising immunofluorescence detection of at least five different target proteins in the sample; b) selecting a region of interest of the sample by comparing the image to a predetermined criterion; c) removing a subsample from the region of interest, and; d) determining a nucleotide sequence of a nucleic acid segment present in the subsample.

21 Claims, 8 Drawing Sheets

(56) References Cited

U.S. PATENT DOCUMENTS

| | | | | |
|---|---|---|---|---|
| 2008/0315119 A1* | 12/2008 | Blackmore | ........ | G01N 21/6428 250/459.1 |
| 2014/0323349 A1* | 10/2014 | Donald | ............ | G01N 33/57434 506/9 |
| 2015/0316482 A1* | 11/2015 | Natarajan | ............ | G01N 33/582 506/9 |
| 2016/0146823 A1* | 5/2016 | Chiu | .................. | G01N 21/6428 506/9 |
| 2016/0314583 A1* | 10/2016 | Couch | .................. | G01N 33/574 |

OTHER PUBLICATIONS

Gibbs, "DNA Annplificatioin by the Polymerase Chain Reaction", Anal. Chem. 1990, 62, 1202-1214.*

* cited by examiner

METHOD OF DETERMINING A NUCLEOTIDE SEQUENCE OF A NUCLEIC ACID SEGMENT FROM A REGION OF INTEREST IN A BIOLOGICAL SAMPLE

TECHNICAL FIELD OF THE INVENTION

The present invention relates to the field of nucleic acid analysis, and more specifically to a method for identification of a region of interest in a biological sample followed by analysis of a nucleic acid present in the region of interest.

BACKGROUND OF THE INVENTION

The analysis of nucleic acids is widely used in clinical and applied fields, as well as in academic research. Biological samples, e.g. tissue samples used for cancer research and diagnosis, frequently contain heterogeneous mixtures of cells. In the research and healthcare field, it is desired to obtain as much information from each subpopulation of a mixed cell population as possible.

There has been a long-felt need in the field to provide more detailed information from trace samples, and this has not been fulfilled by previously known methods.

Removal of regions of interest from microscopic samples followed by DNA sequencing of the removed areas is known from e.g. S J Murphy et al: DNA Res. 19, 395-406 (2012) and the product bulletin "Applied Biosystems Arcturus HistoGene LCM Immunofluorescence Staining Kit" CO14933 0710, Life Technologies Corp. 2010 (https://tools.lifetechnologies.com/content/sfs/brochures/cms_086334.pdf). The selection of the regions of interest is here however based on simple histological staining or single protein immunofluorescence staining and manual identification. There is thus a need in this field for more accurate and objective identification of regions of interest to be subjected to sequencing.

SUMMARY OF THE INVENTION

One aspect of the invention is to provide a method for analysis of a nucleic acid present in a region of interest in a biological sample. This is achieved with a method as defined in claim 1.

The novel method described herein can provide protein expression information for many proteins and add to that DNA sequence information, all from one single more homogeneous subsection of a heterogeneous sample. One advantage is that specific subpopulations of cells within mixed populations can be accurately identified from predetermined selection criteria and analysed. A further advantage is that mutations can be identified, which may be useful for diagnosis and/or prognosis or for further investigation of drug targets.

Further suitable embodiments of the invention are described in the dependent claims.

Definitions

To more clearly and concisely describe and point out the subject matter of the claimed invention, the following definitions are provided for specific terms that are used in the following description and the claims appended hereto.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

As used herein, the term "solid support" refers to an article on which the biological sample may be immobilized and the protein and target nucleic acid sequence may be subsequently detected by the methods disclosed herein. The biological sample may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

As used herein, the term "fluorescent marker" refers to a fluorophore that selectively stains particular subcellular compartments. Examples of suitable fluorescent marker (and their target cells, subcellular compartments, or cellular components if applicable) may include, but are not limited to: 4',6-diamidino-2-phenylindole (DAPI) (nucleic acids), Eosin (alkaline cellular components, cytoplasm), Hoechst 33258 and Hoechst 33342 (two bisbenzimides) (nucleic acids), Propidium Iodide (nucleic acids), Quinacrine (nucleic acids), Fluorescein-phalloidin (actin fibers), Chromomycin A 3 (nucleic acids), Acriflavine-Feulgen reaction (nucleic acid), Auramine 0-Feulgen reaction (nucleic acids), Ethidium Bromide (nucleic acids). Nissl stains (neurons), high affinity DNA fluorophores such as POPO, BOBO, YOYO and TOTO and others, and Green Fluorescent Protein fused to DNA binding protein (e.g., histones), ACMA, and Acridine Orange. Preferably, the fluorescent marker stains the nucleus.

As used herein, the term "fluorophore" refers to a chemical compound, which when excited by exposure to a particular wavelength of light, emits light (at a different wavelength). The terms "fluorescence", "fluorescent", or "fluorescent signal" all refer to the emission of light by an excited fluorophore. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'-disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)4-methylcoumarin, -, 4,4'-diisothiocyanatodihydrostilbene-2,2'-disulfonic acid, 4, 4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron™ Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, and squaraines.

In some embodiments, a fluorophore may essentially include a fluorophore that may be attached to an antibody, for example, in an immunofluorescence analysis. Suitable fluorophores that may be conjugated to a antibody include, but are not limited to, Fluorescein, Rhodamine, Texas Red, Cy2, Cy3, Cy5, VECTOR Red, ELF™ (Enzyme-Labeled Fluorescence), Cy2, Cy3, Cy3.5, Cy5, Cy7, FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1, 3-diazol-4-yl) amino]caproyl] (NBD), BODIPY, boron dipyrromethene difluoride, Oregon Green, MITOTRACKER, Red, DiOC.sub.7 (3), DilC.sub.18, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Lissamine, Umbelliferone, Tyrosine or Tryptophan. In some embodiments, a fluorophore may essentially include a cyanine dye. In some embodiments, a fluorophore may essentially include one or more cyanine dye (e.g., Cy3 dye, a Cy5 dye, or a Cy7 dye).

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab')2, or Fab'). In addition, aggregates, polymers, and conjugates of immunoglobulins or their fragments may be used where appropriate so long as binding affinity for a particular molecule is substantially maintained.

"Target," as used herein, generally refers to the component of a biological sample that may be detected when present in the biological sample. The target may be any substance for which there exists a naturally occurring specific binder (e.g., an antibody), or for which a specific binder may be prepared (e.g., a small molecule binder). In general, the binder may bind to target through one or more discrete chemical moieties of the target or a three-dimensional structural component of the target (e.g., 3D structures resulting from peptide folding). The target may include one or more of peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may include proteins or nucleic acids.

As used herein, the term "binder" refers to a biological molecule that may bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, haptens, and the like. A suitable binder may be selected depending on the sample to be analyzed and the targets available for detection. For example, a target in the sample may include a ligand and the binder may include a receptor or a target may include a receptor and the probe may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant (KA) for the target no lower than about 105 M−1 under ambient conditions (i.e., a pH of about 6 to about 8 and temperature ranging from about 0° C. to about 37° C.).

As used herein, the term "in situ" generally refers to an event occurring in the original location, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

A "chemical agent" may include one or more chemicals capable of modifying the fluorophore or the cleavable linker (if present) between the fluorophore and the binder. A chemical agent may be contacted with the fluorophore in the form of a solid, a solution, a gel, or a suspension. Suitable chemical agents useful to modify the signal include agents that modify pH (for example, acids or bases), electron donors (e.g., nucleophiles), electron acceptors (e.g., electrophiles), oxidizing agents, reducing agents, or combinations thereof. In some embodiments, a chemical agent may include a base, for example, sodium hydroxide, ammonium hydroxide, potassium carbonate, or sodium acetate. In some embodiments, a chemical agent may include an acid, for example, hydrochloric acid, sulfuric acid, acetic acid, formic acid, trifluoroacetic acid, or dichloroacetic acid. In some embodiments, a chemical agent may include nucleophiles, for example, cyanides, phosphines, or thiols. In some embodiments, a chemical agent may include reducing agents, for example, phosphines, thiols, sodium dithionite, or hydrides that can be used in the presence of water such as borohydride or cyanoborohydrides. In some embodiments, a chemical agent may include oxidizing agents, for example, active oxygen species, hydroxyl radicals, singlet oxygen, hydrogen peroxide, or ozone. In some embodiments, a chemical agent may include a fluoride, for example tetrabutylammonium fluoride, pyridine-HF, or SiF4.

One or more of the aforementioned chemical agents may be used in the methods disclosed herein depending upon the susceptibility of the fluorophore, of the binder, of the target, or of the biological sample to the chemical agent. In some embodiments, a chemical agent that essentially does not affect the integrity of the binder, the target, and the biological sample may be employed. In some embodiments, a chemical agent that does not affect the specificity of binding between the binder and the target may be employed.

DETAILED DESCRIPTION OF EMBODIMENTS

Figure 1:
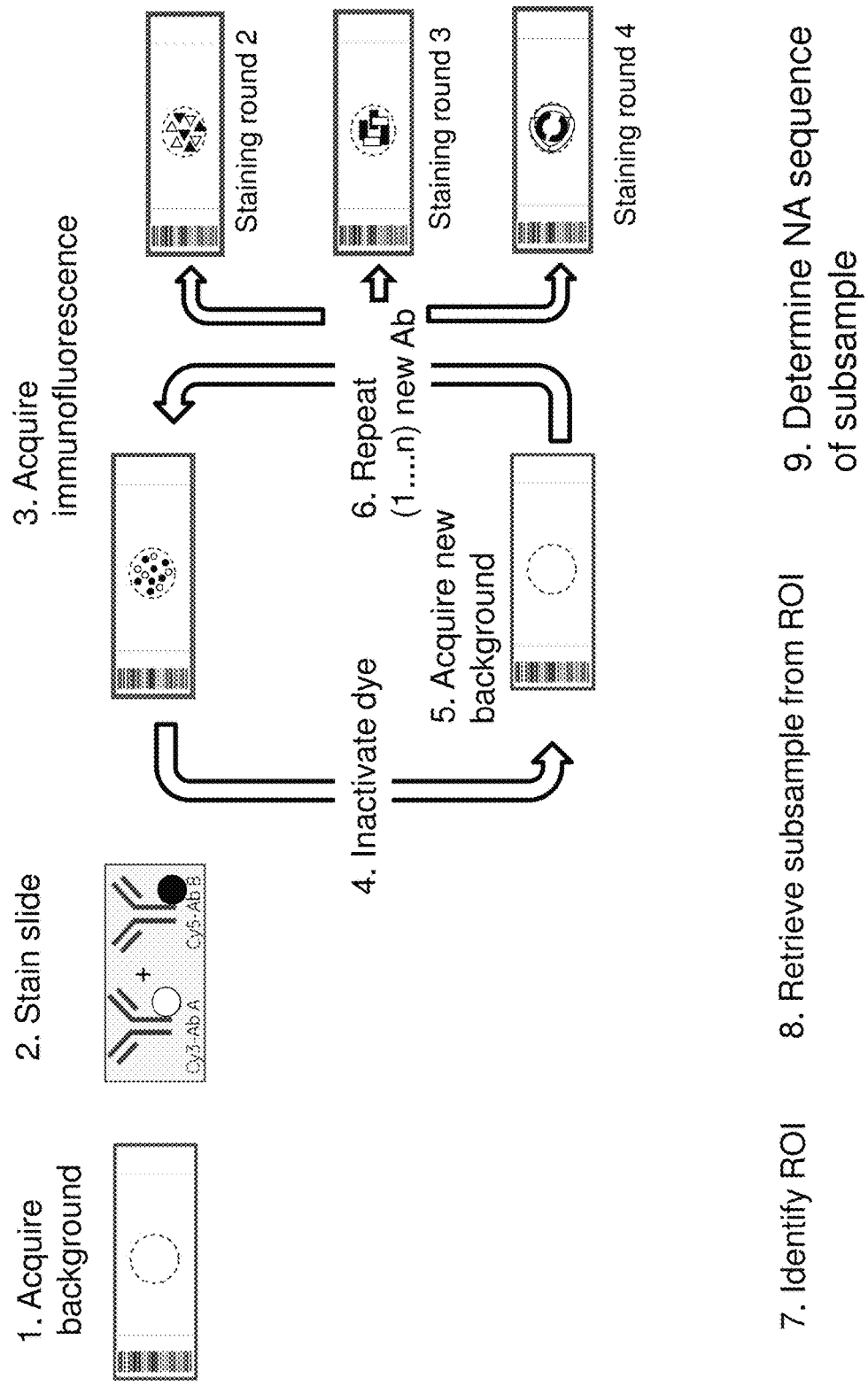
FIG. 1 shows an exemplary workflow of the method of the invention.
Figure 2:
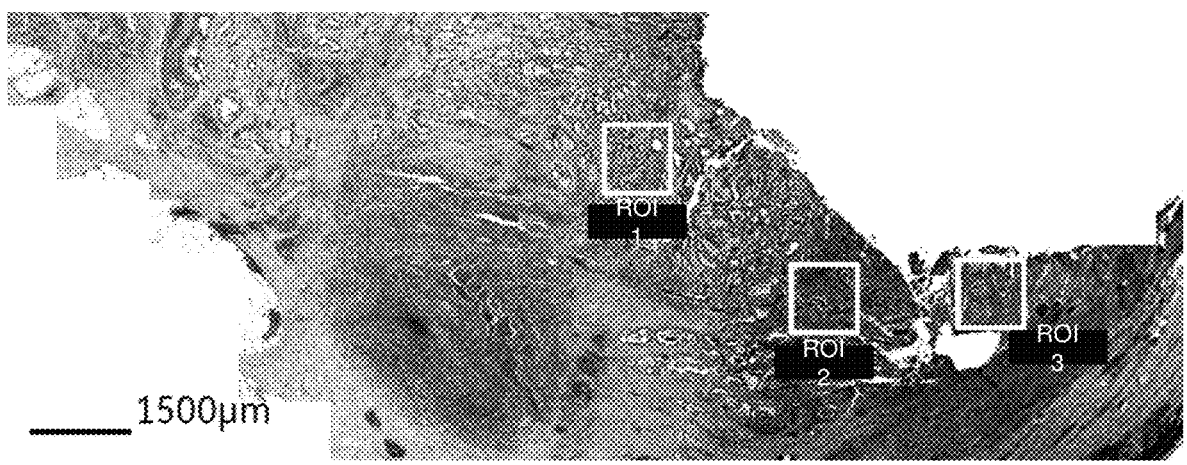
FIG. 2 shows an overview of a FFPE tissue section with three regions of interest marked.
Figure 3:
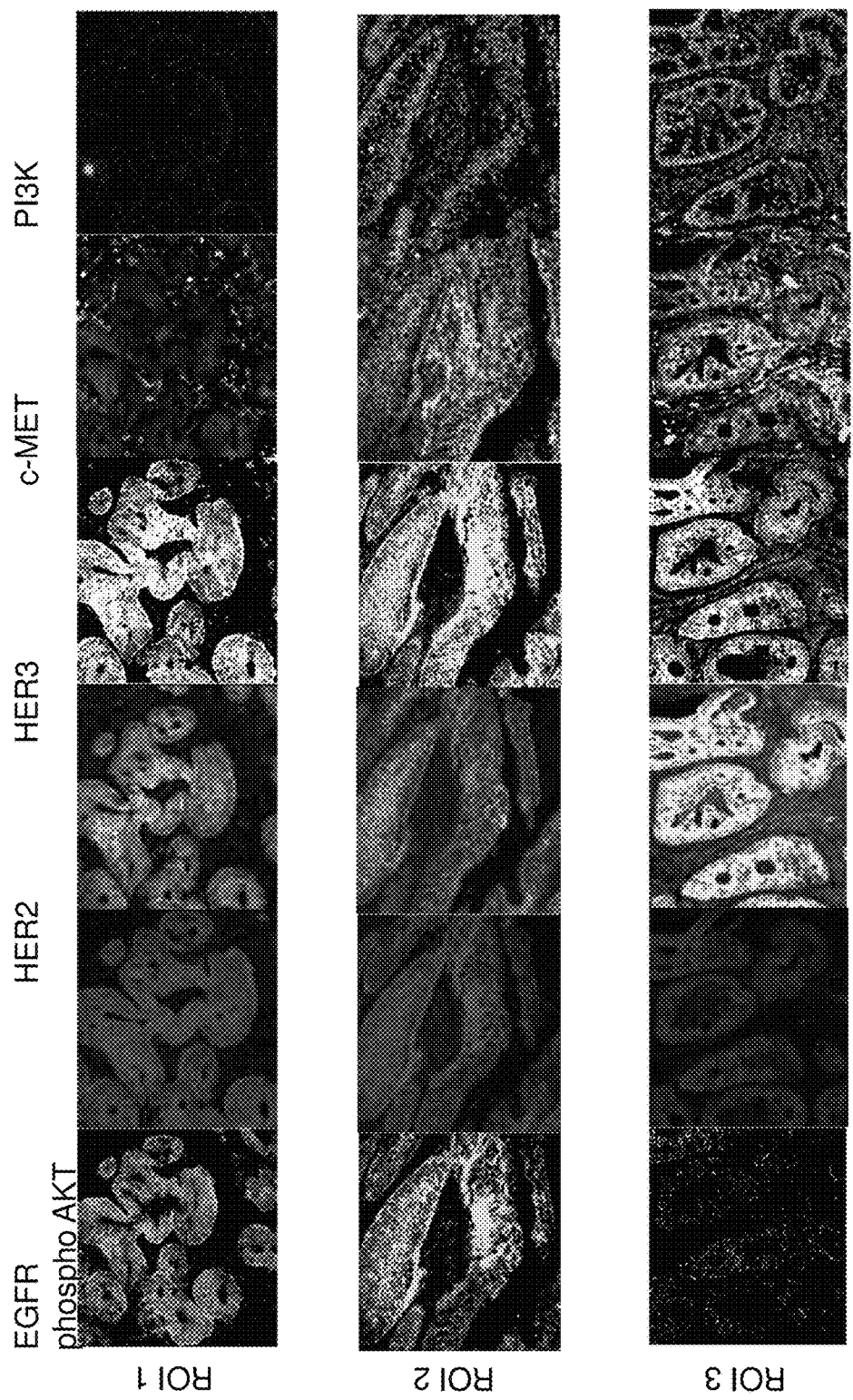
FIG. 3 shows, for each of the three regions of interest, the individual immunofluorescence signals for fluorescent antibodies towards the target proteins EGFR, HER2, HER3, c-MET, PI3K and phosphorylated AKT.
Figure 4:
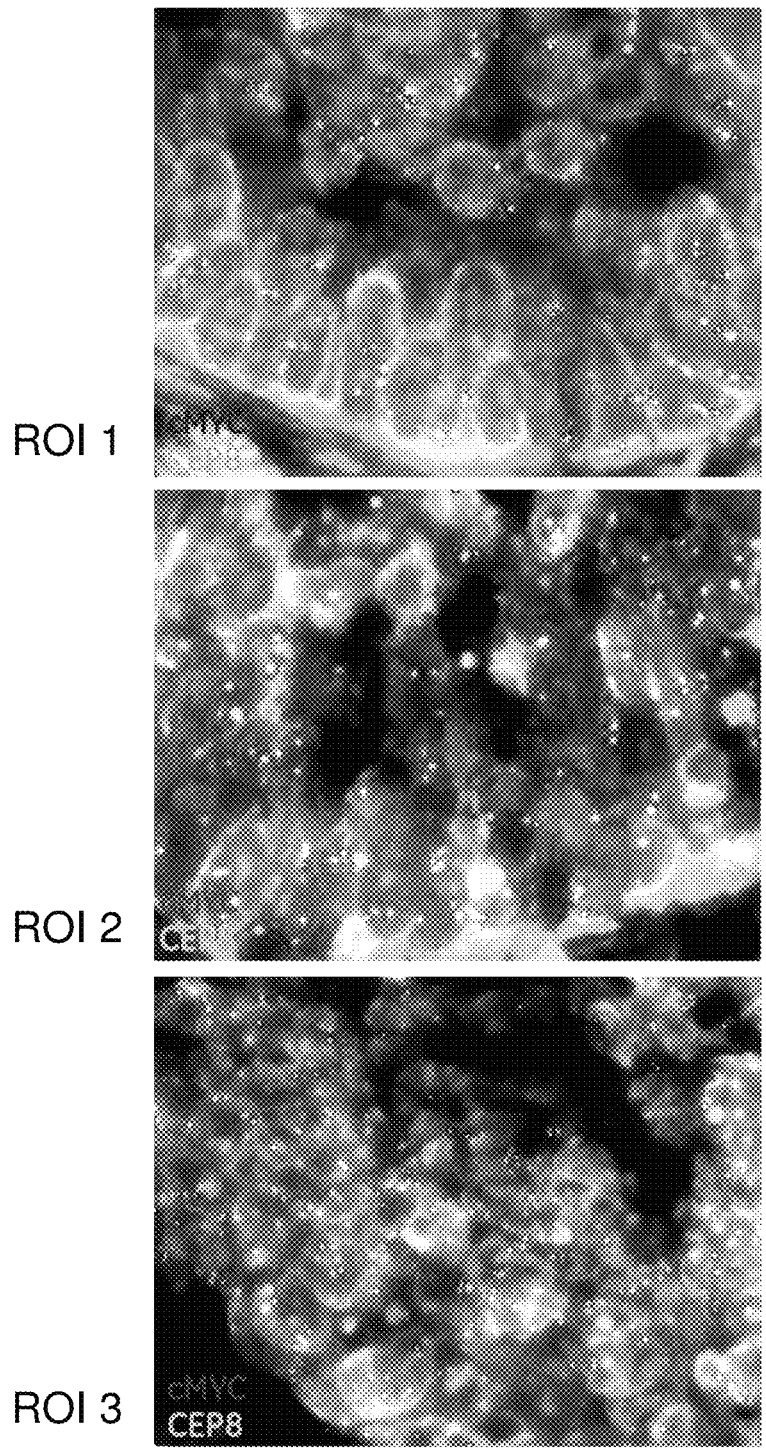
FIG. 4 shows overlaid images with c-MYC and CEP8 FISH fluorescence signals from the three regions of interest ROI 1-3.
Figure 5:
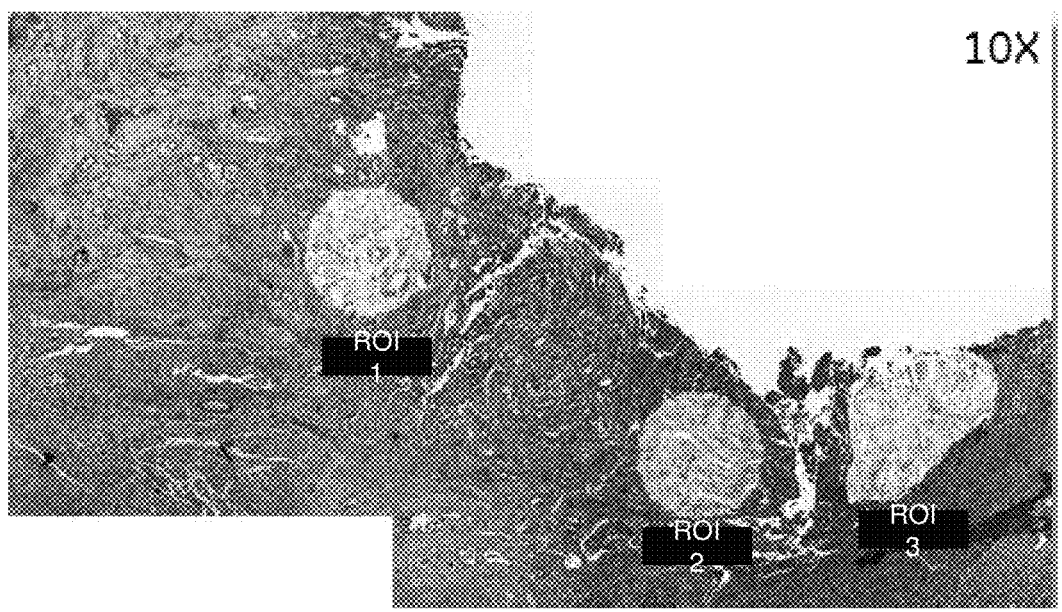
FIG. 5 shows an overview of the FFPE tissue section after removal of subsamples from the three regions of interest.

In one aspect the present invention discloses a method for determining a nucleotide sequence of a nucleic acid segment present in a biological sample, such as a microscopy sample. The sample can e.g. be a tissue section, such as a formalin-fixed paraffin-embedded (FFRPE) section, but it can also be e.g. a smear or a preparation derived from a fluid sample. Suitably, the sample may be affixed to or otherwise mounted on a solid support, such as a microscope slide, e.g. a glass or quartz slide. The solid support or microscope slide can suitably have a positively charged surface, e.g. an aminosilane or polylysine coating, which improves the adherence of the sample to the support/slide during subsequent staining and bleaching steps. An example of a positively charged support/slide is the Superfrost Plus slides, available from Thermo Scientific. The solid support or microscope slide can also suitably have a low autofluorescence, e.g. with an autofluorescence intensity which is less than 1% or less than 0.1% of the average fluorescence intensity over a region of interest in the sample. Standard low-fluorescence glass or quartz qualities used for fluorescence microscopy slides are suitable from this point of view.

The method comprises the steps of a)-d) as outlined below:

a) generating a fluorescent image of the sample by a protocol comprising immunofluorescence detection of at least five different target proteins in the sample. The immunofluorescence detection can suitably involve a plurality of incubations of the sample with fluorophore-conjugated antibodies against the target proteins.

b) identifying and/or selecting a region of interest of the sample by comparing the image to a predetermined criterion. This predetermined criterion can e.g. be a pattern of expression levels for the different proteins. The pattern may be qualitative (e.g. combinations of high/low expression of different proteins), semiquantitative (e.g. combinations of expressions above or below certain threshold levels) or quantitative (e.g. involving multivariate correlations).

c) removing a subsample from the region of interest. This can suitably be performed while the sample is still affixed to the same solid support/microscope slide as in steps a) and b).

d) determining a nucleotide sequence of a nucleic acid segment present in the subsample. The nucleic acid segment may be a nucleic acid or part of a nucleic acid. The nucleic acid may be DNA or it may be RNA.

In certain embodiments step a) comprises generating a plurality of fluorescent images of the sample, each image being generated by a protocol comprising immunofluorescence detection of at least one target protein in the sample and fluorescence detection of at least one morphological feature in said sample. The detection of one or more morphological features allows the localization of the same regions of interest throughout the different images of the sample, either by direct alignment of the different images or by the provision of navigational information such as a common coordinate system for the different images. The detection of morphological features can be accomplished by staining with a fluorescent marker, as described below, or alternatively from autofluorescence of the sample or by the introduction of e.g. fluorescent particles in the sample. The plurality of fluorescent images can e.g. be obtained by repeated cycles of i) immunofluorescence staining, ii) capture of an immunofluorescent image and iii) bleaching of the sample. The immunofluorescence staining can comprise contacting the sample with at least one antibody against at least one target protein, which antibody/antibodies is/are conjugated with a fluorophore. The staining can e.g. comprise contacting the sample with two antibodies against two different target proteins, where each antibody is conjugated with a different fluorophore, producing fluorescence detectable at two different wavelengths. It is also possible to use a non-conjugated antibody in combination with a fluorophore-labeled antibody against the non-conjugated antibody. Examples of suitable fluorophores are cyanine dyes, such as Cy3 (I) and/or Cy5 (II), where the R1 and R2 groups can independently of each other be e.g. methyl, ethyl, propyl, butyl, carboxyl, acetylmethoxy, sulfo or N.hydroxysuccinimide groups. The Cy3 and Cy5 fluorophores can be conveniently bleached by the procedures discussed below.

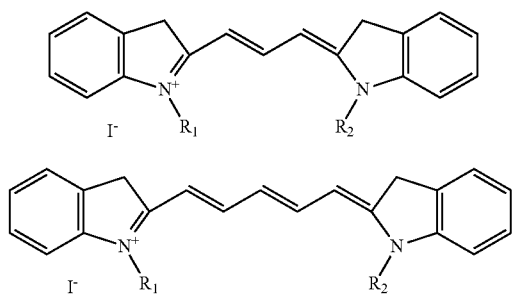

The bleaching of the sample allows the extinguishment of the fluorescence signals from the previous immunofluorescence staining, such that the sample can be stained again with another fluorophore-conjugated antibody without cross-talk from the previous staining. The bleaching can e.g. be a chemical inactivation procedure, involving incubation with one or more chemical agents, e.g. oxidants such as hydrogen peroxide as disclosed in U.S. Pat. No. 7,741,046, it can be a photobleaching procedure or it can be a photoassisted chemical inactivation, e.g. as disclosed in U.S. Pat. No. 8,568,991 where triphenylborate lithium salt was used as a chemical agent in combination with light irradiation. In particular, the bleaching may comprise contacting the sample with a peroxide, such as hydrogen peroxide, or with an organic borate, such as an aromatic borate like triphenyl monobenzyl borate. Although nucleic acids are sensitive to oxidative degradation, surprisingly no substantial degradation has been observed after the bleaching. Without being bound by theory, it can be speculated that the DNA is shielded from the chemical agent, possibly by complexation with proteins.

In certain embodiments, the biological sample is subjected to an antigen retrieval step before step a). The purpose of the antigen retrieval step is to break crosslinks in the sample, particularly crosslinks introduced by previous formaldehyde fixation processes. This improves the binding of the antibodies introduced in step a) with the target proteins in the sample. The antigen retrieval step may comprise heating in a non-neutral buffer (i.e. a buffer with pH 6.5 or lower or pH 7.5 or higher), e.g. a buffer having a pH of 5-6.5 or 8-9.5. Suitable such buffers include Bond Epitope Retrieval Solution (Leica Biosystems).

In some embodiments of the method, the fluorescent image generated in step a) is a composite image obtained by overlaying a plurality of immunofluorescent images of the sample obtained as described above. The overlaying can be accomplished by using fluorescent signals from morphological features in the sample as a navigational aid for the alignment of the individual images.

In certain embodiments, the sample is further stained with a fluorescent marker that provides the morphological information as discussed above. This fluorescent marker can suitably be a nucleus stain, such as 4',6-diamidino-2-phenylindole (DAPI) or other nucleic acid markers as listed under Definitions.

In some embodiments, the at least five different target proteins comprise at least one of EGFR (epidermal growth factor receptor), HER2 (human epidermal growth factor receptor 2), HER3 (human epidermal growth factor receptor 3), the receptor tyrosine kinase c-MET, phosphoinositide 3-kinase (PI3K), phosphorylated protein kinase B (AKT), ribosomal protein S6 (S6), phosphorylated extracellular signal regulating kinases 1 and 2 (phospho ERK1/2), cytokeratin PCK-26 (PCK26), anion transport protein AE1 (AE1) and sodium-potassium adenosinetriphosphatase (NaKATPase). The at least five different target proteins may also, or alternatively, comprise any one of the target proteins listed below under the separate heading Target proteins.

In certain embodiments of the method, step a) further comprises fluorescence in situ hybridization (FISH) staining of the sample followed by capture of a fluorescent hybridization image and overlaying of the fluorescent hybridization image with the immunofluorescent images. The FISH staining may comprise contacting the sample with an oligonucleotide (probe) capable of hybridizing with a target nucleic acid region/sequence in the sample, conjugated with a fluorophore. Examples of such target nucleic acid regions/sequences can be the c-MYC gene or the centromeric region of chromosome 8 (CEP8). Further examples are discussed below under Target nucleic acid sequences.

In some embodiments, step c) of the method involves removing the subsample by laser microdissection. Laser microdissection is a technique where a laser beam is used to either cut out a subsample (typically a UV laser) or to melt a polymer film that adheres to the subsample (typically an IR laser). Commercially available laser microdissection instruments are e.g. Life Technologies Arcturus and Leica LMD. Alternatively, the subsample may be removed using micromilling. In this technique the subsample is removed using a rotating milling tool controlled by a precision x-y table. Commercially available micromilling instruments include MilliSect and MillMan from AvanSci Bio/Roche. The circle-equivalent diameter of the subsample removed can suitably be less than 2 mm, such as about 5 to about 1500 micrometers.

In step d), the sequence determination can be performed directly on the removed sample, using methods such as ion semiconductor sequencing (also called ion torrent sequencing) or e.g. Illumina dye sequencing. It is however also possible to perform an amplification step before sequencing. Such amplification may be performed by methods known in the art, e.g. PCR, multiple displacement amplification (MDA) or rolling circle amplification (RCA). Ion semiconductor sequencing involves detection of hydrogens released upon polymerase-induced incorporation of a nucleotide in a strand of DNA by a semiconductor chip. Examples of instrumentation for this technique includes Life Technologies Ion Torrent. Illumina dye sequencing involves fluorescence detection of the incorporation of labeled nucleotides in a strand of DNA and is exemplified by the Illumina instruments available from Illumina.

Biological Samples

A biological sample in accordance with one embodiment of the invention may be solid or fluid. Biological sample refers to a sample obtained from a biological subject, including sample of biological tissue or fluid origin obtained in vivo or in vitro. Suitable examples of biological samples may include, but are not limited to, blood, saliva, cerebral spinal fluid, pleural fluid, milk, lymph, sputum, semen, urine, stool, tears, needle aspirates, external sections of the skin, respiratory, intestinal, and genitourinary tracts, tumors, organs, cell cultures, or solid tissue sections. In some embodiments, the biological sample may be analyzed as is, that is, without harvest and/or isolation of the target of interest. In an alternate embodiment, harvest of the sample may be performed prior to analysis. In some embodiments, the methods disclosed herein may be particularly suitable for in-vitro analysis of biological samples. Biological samples may be immobilized on a solid support, such as in glass slides, microtiter, or ELISA plates.

A biological sample may include any of the aforementioned samples regardless of their physical condition, such as, but not limited to, being frozen or stained or otherwise treated. In some embodiments, a biological sample may include compounds which are not naturally intermixed with the sample in nature such as preservatives, anticoagulants, buffers, fixatives, nutrients, antibiotics, or the like.

A biological sample may be of prokaryotic origin or eukaryotic origin (e.g., insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee or human).

In some embodiments, a biological sample may include a tissue sample, a whole cell, a cell constituent, a cytospin, or a cell smear. In some embodiments, a biological sample essentially includes a tissue sample. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

The tissue sample may be obtained by a variety of procedures including, but not limited to surgical excision, aspiration or biopsy. In some embodiments, the tissue sample may be fixed and embedded in paraffin. The tissue sample may be fixed or otherwise preserved by conventional methodology; the choice of a fixative may be determined by the purpose for which the tissue is to be histologically stained or otherwise analyzed. The length of fixation may depend upon the size of the tissue sample and the fixative used. For example, neutral buffered formalin, Bouin's or paraformaldehyde, may be used to fix or preserve a tissue sample.

In some embodiments, a biological sample includes tissue sections of normal or cancerous origin, such as tissue sections form colon, breast, prostate, lung, liver, and stomach. A tissue section may include a single part or piece of a tissue sample, for example, a thin slice of tissue or cells cut from a tissue sample. In some embodiments, multiple sections of tissue samples may be taken and subjected to analysis, provided the methods disclosed herein may be used for analysis of the same section of the tissue sample with respect to at least two different targets (i.e., one of these being of a protein origin and another one being a nucleic acid origin). A tissue section, if employed as a biological sample may have a thickness in a range that is less than about 100 micrometers, in a range that is less than about 50 micrometers, in a range that is less than about 25 micrometers, or in range that is less than about 10 micrometers.

Target Proteins

A target protein according to an embodiment of the invention may be present on the surface of a biological sample (for example, an antigen on a surface of a tissue section) or present in the bulk of the sample (for example, an antibody in a buffer solution). In some embodiments, a target protein may not be inherently present on the surface of a biological sample and the biological sample may have to be processed to make the target protein available on the surface. In some embodiments, the target protein may be in a tissue, either on a cell surface, or within a cell.

Suitability of target protein to be analyzed may be determined by the type and nature of analysis required for the biological sample. In some embodiments, a target may provide information about the presence or absence of an analyte in the biological sample. In another embodiment, a target protein may provide information on a state of a biological sample. For example, if the biological sample includes a tissue sample, the methods disclosed herein may be used to detect target protein that may help in comparing different types of cells or tissues, comparing different developmental stages, detecting the presence of a disease or abnormality, or determining the type of disease or abnormality.

Suitable target proteins may include one or more of peptides, proteins (e.g., antibodies, affibodies, or aptamers), enzymes, ligands, receptors, antigens, or haptens. One or more of the aforementioned target proteins may be characteristic of particular cells, while other target proteins may be associated with a particular disease or condition. In some embodiments, target proteins in a tissue sample that may be detected and analyzed using the methods disclosed herein may include, but are not limited to, prognostic markers, predictive markers, hormone or hormone receptors, lymphoids, tumor markers, cell cycle associated markers, neural tissue and tumor markers, or cluster differentiation markers.

Suitable examples of prognostic markers may include enzymatic targets such as galactosyl transferase II, neuron specific enolase, proton ATPase-2, or acid phosphatase. Other examples of prognostic protein or gene markers include Ki67, cyclin E, p53, cMet.

Suitable examples of predictive markers (drug response) may include protein or gene targets such as EGFR, Her2, ALK.

Suitable examples of hormone or hormone receptors may include human chorionic gonadotropin (HCG), adrenocorticotropic hormone, carcinoembryonic antigen (CEA), prostate-specific antigen (PSA), estrogen receptor, progesterone receptor, androgen receptor, gClq-R/p33 complement receptor, IL-2 receptor, p75 neurotrophin receptor, PTH receptor, thyroid hormone receptor, or insulin receptor.

Suitable examples of lymphoids may include alpha-1-antichymotrypsin, alpha-1-antitrypsin, B cell target, bcl-2, bcl-6, B lymphocyte antigen 36 kD, BM1 (myeloid target), BM2 (myeloid target), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage target, muramidase (lysozyme), p80 anaplastic lymphoma kinase, plasma cell target, secretory leukocyte protease inhibitor, T cell antigen receptor (JOVI 1), T cell antigen receptor (JOVI 3), terminal deoxynucleotidyl transferase, or unclustered B cell target.

Suitable examples of tumor markers may include alpha fetoprotein, apolipoprotein D, BAG-1 (RAP46 protein), CA19-9 (sialyl lewisa), CA50 (carcinoma associated mucin antigen), CAl25 (ovarian cancer antigen), CA242 (tumour associated mucin antigen), chromogranin A, clusterin (apolipoprotein J), epithelial membrane antigen, epithelial-related antigen, epithelial specific antigen, gross cystic disease fluid protein-15, hepatocyte specific antigen, heregulin, human gastric mucin, human milk fat globule, MAGE-1, matrix metalloproteinases, melan A, melanoma target (HMB45), mesothelin, metallothionein, microphthalmia transcription factor (MITF), Muc-1 core glycoprotein. Muc-1 glycoprotein, Muc-2 glycoprotein, Muc-5AC glycoprotein, Muc-6 glycoprotein, myeloperoxidase, Myf-3 (Rhabdomyosarcoma target), Myf-4 (Rhabdomyosarcoma target), MyoD1 (Rhabdomyosarcoma target), myoglobin, nm23 protein, placental alkaline phosphatase, prealbumin, prostate specific antigen, prostatic acid phosphatase, prostatic inhibin peptide, PTEN, renal cell carcinoma target, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, or von Willebrand factor.

Suitable examples of cell cycle associated markers may include apoptosis protease activating factor-1, bcl-w, bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mc1-1, minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, or topoisomerase II beta.

Suitable examples of neural tissue and tumor markers may include alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma target, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, serotonin, SNAP-25, synapsin I, synaptophysin, tau, tryptophan hydroxylase, tyrosine hydroxylase, or ubiquitin.

Suitable examples of cluster differentiation markers may include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, LD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148, CDw149, CDw150, CD151, CD152, CD153, CD154, CD155, CD156, CD157, CD158a, CD158b, CD161, CD162, CD163, CD164, CD165, CD166, and TCR-zeta.

Other suitable target proteins include centromere protein-F (CENP-F), giantin, involucrin, lamin A&C (XB 10), LAP-70, mucin, nuclear pore complex proteins, p180 lamellar body protein, ran, cathepsin D, Ps2 protein, Her2-neu, P53, S100, epithelial target antigen (EMA), TdT, MB2, MB3, PCNA, Ki67, cytokeratin, PI3K, cMyc or MAPK.

Still other suitable target proteins include Her2/neu (epidermal growth factor over expressed in breast and stomach cancer, therapy by a monoclonal antibody slows tumor growth); EGF-R/erbB (epidermal growth factor receptor); ER (estrogen receptor required for growth of some breast cancer tumors, located in the nucleus and detected with ISH for deciding on therapy limiting estrogen in positive patients); PR (progesterone receptor is a hormone that binds to DNA); AR (androgen receptor is involved in androgen dependent tumor growth); β-catenin (oncogene in cancer translocates from the cell membrane to the nucleus, which functions in both cell adhesion and as a latent gene regulatory protein); Phospho-β-Catenin: phosphorylated (form of β-catenin degrades in the cytosol and does not translocate to the nucleus); GSK3β (glycogen synthase kinase-3β protein in the Wnt pathway phosphorylates β-catenin marking the phospo-β-catenin for rapid degradation in the protostomes); PKCβ (mediator G-protein coupled receptor); NFKβ (nuclear factor kappa B marker for inflammation when translocated to the nucleus); VEGF (vascular endothelial growth factor related to angiogenesis); E-cadherin (cell to cell interaction molecule expressed on epithelial cells, the function is lost in epithelial cancers); c-met (tyrosine kinase receptor). In a preferred embodiment, the target protein is HER2.

Target Nucleic Acid Sequences

A target nucleic acid sequence according to an embodiment of the invention refers to a sequence of interest which is contained in a nucleic acid molecule in the biological sample. The nucleic acid molecule may be present in the nuclei of the cells of the biological sample (for example, chromosomal DNA) or present in the cytoplasm (for example, mRNA). In some embodiments, a nucleic acid molecule may not be inherently present on the surface of a biological sample and the biological sample may have to be processed to make the nucleic acid molecule accessible by a probe. For example, protease treatment of the sample could readily bring the target nucleic acid sequences.

Suitability of a nucleic acid molecule to be analyzed may be determined by the type and nature of analysis required for the biological sample. In some embodiments, the analysis may provide information about the gene expression level of the target nucleic acid sequence in the biological sample. In other embodiments, the analysis may provide information on the presence or absence or amplification level of a chromosomal DNA. For example, if the biological sample includes a tissue sample, the methods disclosed herein may be used to detect a target nucleic acid sequence that may identify cells which has an increased copy number of a particular chromosomal segment harboring the target nucleic acid sequence.

In some embodiments, the target nucleic acid sequence in a tissue sample that may be detected and analyzed using the methods disclosed herein may include, but are not limited to, nucleic acid sequences for prognostic markers, hormone or hormone receptors, lymphoids, tumor markers, cell cycle associated markers, neural tissue and tumor markers, or cluster differentiation markers. Examples of these markers are described in the section entitled "Target proteins". For example, in one embodiment, the target nucleic acid sequence target is a sequence for the EGFR, TOP2A, cMyc, ALK, FGFR1 or HER2 gene.

In certain embodiments, the target nucleic acid sequence includes a sequence that is part of the gene sequence which encodes the target protein. In other embodiments, the target nucleic acid sequence does not include a sequence that is part of the gene sequence which encodes the target protein. Thus, the target nucleic acid sequence may include a sequence that is part of the gene sequence which encodes a different protein than the target protein.

Probes for the Target Nucleic Acid Sequences

In some embodiments, a probe is used to detect the target nucleic acid sequences. It is desirable that the probe binds specifically to the region of nucleic acid molecule that contains the sequence of interest. Thus, in some embodiments, the probe is sequence-specific. A sequence-specific probe may include a nucleic acid and the probe may be capable of recognizing a particular linear arrangement of nucleotides or derivatives thereof. In some embodiments, the linear arrangement may include contiguous nucleotides or derivatives thereof that may each bind to a corresponding complementary nucleotide in the probe. In an alternate embodiment, the sequence may not be contiguous as there may be one, two, or more nucleotides that may not have corresponding complementary residues on the probe. Suitable examples of probes may include, but are not limited to DNA or RNA oligonucleotides or polynucleotides, peptide nucleic acid (PNA) sequences, locked nucleic acid (LNA) sequences, or aptamers. In some embodiments, suitable probes may include nucleic acid analogs, such as dioxygenin dCTP, biotin dcTP 7-azaguanosine, azidothymidine, inosine, or uridine.

In some embodiments, a probe may form a Watson-Crick bond with the target nucleic acid sequence. In another embodiment, the probe may form a Hoogsteen bond with the target nucleic acid sequence, thereby forming a triplex. A probe that binds by Hoogsteen binding may enter the major groove of a nucleic acid sequence and hybridizes with the bases located there. In certain embodiments, the probes may form both Watson-Crick and Hoogsteen bonds with the target nucleic acid sequence (for example, bis PNA probes are capable of both Watson-Crick and Hoogsteen binding to a nucleic acid molecule).

In some embodiments, the probe may comprise a nucleic acid probe, a peptide nucleic acid probe, a locked nucleic acid probe, mRNA probe, miRNA probe or siRNA probe.

The length of the probe may also determine the specificity of binding. The energetic cost of a single mismatch between the probe and the target nucleic acid sequence may be relatively high for shorter sequences than for longer ones. In some embodiments, hybridization of smaller probes may be more specific than the hybridization of longer probes, as the longer probes may be more amenable to mismatches and may continue to bind to the nucleic acid depending on the conditions. In certain embodiments, shorter probes may exhibit lower binding stability at a given temperature and salt concentration. Probes that may exhibit greater stability to bind short sequences may be employed in this case (for examples, bis PNA). In some embodiments, the probe may have a length in range of from about 4 nucleotides to about 12 nucleotides, from about 12 nucleotides to about 25 nucleotides, from about 25 nucleotides to about 50 nucleotides, from about 50 nucleotides to about 100 nucleotides, from about 100 nucleotides to about 250 nucleotides, from about 250 nucleotides to about 500 nucleotides, or from about 500 nucleotides to about 1000 nucleotides. In some embodiments, the probe may have a length in a range that is greater than about 1000 nucleotides. Notwithstanding the length of the probe, all the nucleotide residues of the probe may not hybridize to complementary nucleotides in the target nucleic acid sequence. For example, the probe may include 50 nucleotide residues in length, and only 25 of those residues may hybridize to the target nucleic acid sequence. In some embodiments, the nucleotide residues that may hybridize may be contiguous with each other. The probe may be single stranded or may include a secondary structure.

In some embodiments, a biological sample may include a cell or a tissue sample and the biological sample may be subjected to in situ hybridization (ISH) using a probe. In some embodiments, a tissue sample may be subjected to in situ hybridization in addition to immunofluorescence (IF) to obtain desired information regarding the tissue sample.

Regardless of the type of probe and the target nucleic acid sequence, the specificity of binding between the probe and the nucleic acid sequence may also be affected depending on the binding conditions (for example, hybridization conditions in case of complementary nucleic acids. Suitable binding conditions may be realized by modulating one or more of pH, temperature, or salt concentration.

A probe may be intrinsically labeled (fluorophore attached during synthesis of probe) with a fluorophore or extrinsically labeled (fluorophore attached during a later step). For example, an intrinsically labeled nucleic acid may be synthesized using methods that incorporate fluorophore-labeled nucleotides directly into the growing nucleic acid chain. In some embodiments, a probe may be synthesized in a manner such that fluorophores may be incorporated at a later stage. For example, this latter labeling may be accomplished by chemical means by the introduction of active amino or thiol groups into nucleic acids chains. In some embodiments, a probe such a nucleic acid (for example, a DNA) may be directly chemically labeled using appropriate chemistries for the same.

EXAMPLES

Example 1

A formalin-fixed paraffin-embedded (FFPE) tumor tissue section sample of 4-5 micrometers thickness (one of several serial sections of a single colorectal cancer tissue block purchased from Pantomics Inc, USA) mounted on a microscope slide (Thermo Scientific Superfrost Plus) having a tissue-retaining positively charged surface treatment was deparaffinized by passage through xylene, then re-hydrated by passage through ethanol followed by a series of water-ethanol mixtures with decreasing ethanol concentration and finally washed with PBS. Next, the slide was subjected to antigen retrieval procedure by heating the slide in Bond Epitope Retrieval solution (Leica) at 100° C. for 20 min. The slide was then stained with S6 antibody conjugated with Cy5 combined with phospho ERK1/2 rabbit antibody and anti-rabbit antibody conjugated with Cy3, followed by counterstaining with DAPI. The slide was coverslipped and the entire slide was imaged using a fluorescence microscope equipped with a 1.25× magnification objective and a DAPI filterset. The images were captured using a digital monochrome camera, and then combined to form one stitched image of the entire slide. From this stitched full slide image the location of the tissue section was determined and coordinates for imaging the tissue section were recorded.

20× images of the tissue section area were then collected using DAPI, Cy3 and Cy5 filtersets to get images specific for nuclei, S6 and phospho ERK1/2 protein staining respectively. These individual markers were stitched to form one image and then overlaid to form a fluorescence pseudocolour image.

The slide was then subjected to a dye inactivation procedure with hydrogen peroxide as described more fully in U.S. Pat. No. 7,741,046 "SEQUENTIAL ANALYSIS OF BIOLOGICAL SAMPLES", herein incorporated by reference in its entirety, and stained with antibodies for EGFR and PI3K conjugated with Cy5 and Cy3 respectively and was counterstained with DAPI. The tissue section was aligned so that images would be collected on the same regions as on the previous round, and imaged again using 20× magnification on each fluorescence channel as above. The inactivation, staining and imaging procedure was then repeated in a third round with Cy3- and Cy5-conjugated antibodies for HER3 and phosphorylated AKT respectively. In a fourth round the procedure was repeated with Cy5-HER2 antibody, Cy3-PCK26 antibody and Cy3-AE1 antibody and in a fifth round, Cy5-c-MET antibody and Cy3-NaKATPase antibody were used.

The slide was then subjected to a 10 min treatment with 0.05% pepsin that partially removed protein structures to allow access to nuclear DNA. The slide was then fixed using aqueous 4% formaldehyde solution for 10 min, washed and subjected to hybridization using FISH probes for the c-MYC gene labeled with Orange (captured on Cy3) and for the CEP8 centromer labeled with Green (captured on FITC).

Sections of all image rounds were then registered using DAPI images of each of the imaging round sets to align the images and they were combined in single filed images to allow simultaneous visualization of the expression of the target proteins EGFR, HER2, HER3, c-MET, PI3K and phosphor-AKT, as well as the presence of c-MYC and CRP8 in the cells.

Based on the protein expressions and the gene presence, four regions of interest, ROI 1-4 (only ROI 1-3 shown in the Figs) were identified. ROI1 had a high expression of EGFR and a low expression of phospho AKT, ROI2 had high expression of both EGFR and phospho AKT, while ROI3 had low expression of EGFR and high expression of phospho AKT.

Figure 6:
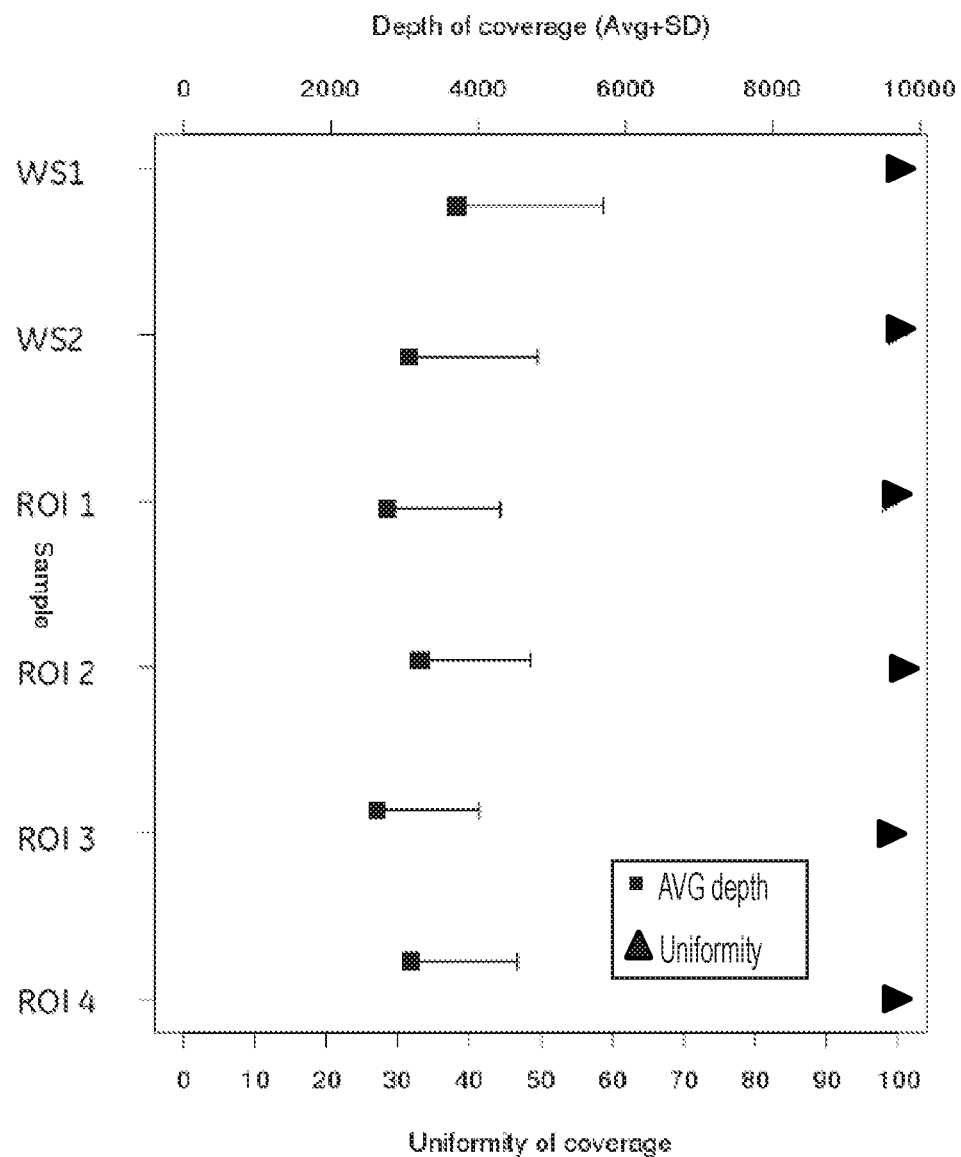
FIG. 6 shows the average depth of coverage and the uniformity of coverage for subsamples from four regions of interest, denoted ROI1, ROI2, ROI3 and ROI4. WS 1 and WS2 are whole slide extractions, used as controls.

The slide was then moved to a Life Technologies Arcturus XT laser capture microdissector (LCM) and a 1.5 mm diameter subsample was retrieved for each region of interest. The subsamples were efficiently retrieved despite the tissue-retaining surface on the slide. Each subsample, containing approx. 10 ng genomic DNA, was then subjected to DNA sequencing in a Life Technologies Ion Torrent ion semiconductor sequencer using an AmpliSeq cancer panel consisting of 740 mutational hotspots in 46 cancer-related genes. As shown by FIG. 6, the depth of coverage was well above 2000× for every ROI and the uniformity of coverage was close to 100%. Table 1 shows more detailed information about the sequencing results for ROI 1-3. Surprisingly, the DNA was found not to be degraded by the dye inactivation procedure (bleaching).

TABLE 1

| ROI # | Mapped reads | AQ20 reads | Mean depth | On target | Uniformity |
| --- | --- | --- | --- | --- | --- |
| 1 | 616 339 | 464 865 | 2 755 | 98.83% | 98.53% |
| 2 | 721 657 | 549 639 | 3 203 | 98.60% | 99.96% |
| 3 | 589 877 | 435 620 | 2 612 | 98.57% | 98.54% |

Example 2

Figure 7:
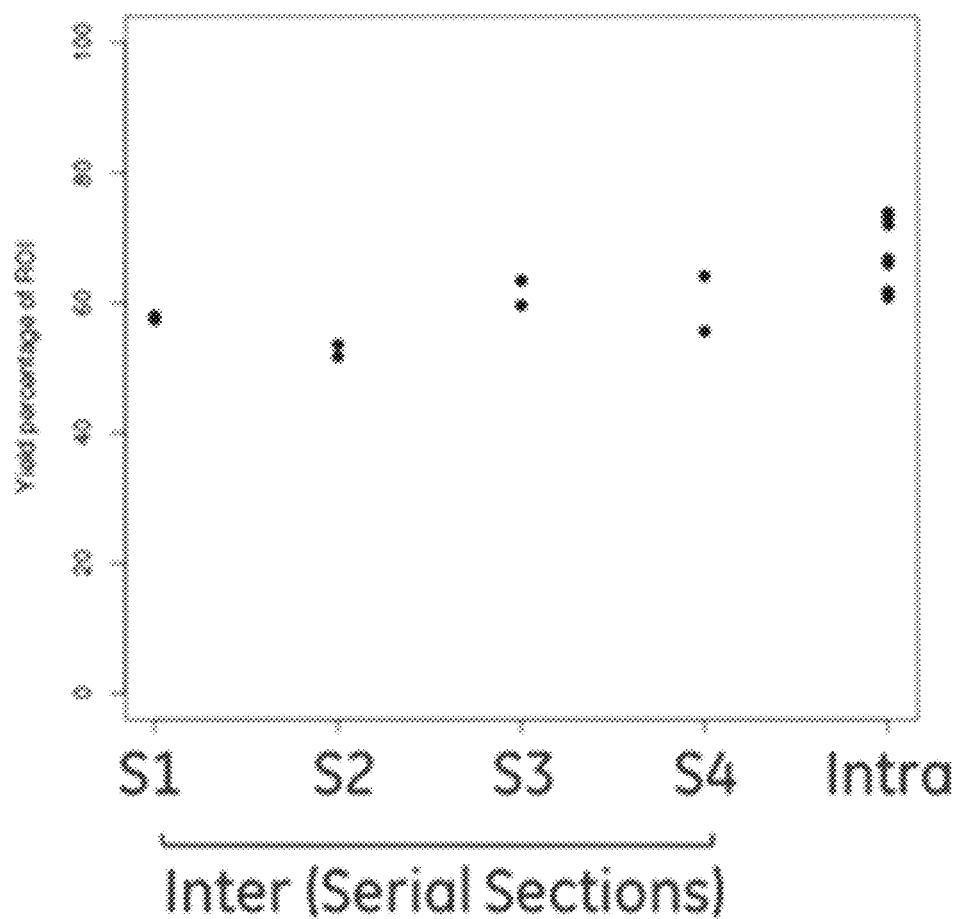
FIG. 7 shows the intersection and intrasection variation of the retrieval yield for subsamples retrieved with a laser capture microdissector.

In order to check the reproducibility of the subsample retrieval step, five serial sections (S1-S5) of the same FFPE tissue block as in Example 1 were stained as in Example 1. From each section two or four 1 mm circular subsamples were retrieved with the LCM and the fluorescence intensity was measured on the slide both in the location from which the subsample had been removed and in the surrounding area. The ratio between the intensities was calculated and used as a measure of the retrieval yield. As shown in FIG. 7, the yield was consistently within the 50-75% interval both for the intersection and intrasection variation.

Example 3

Figure 8:
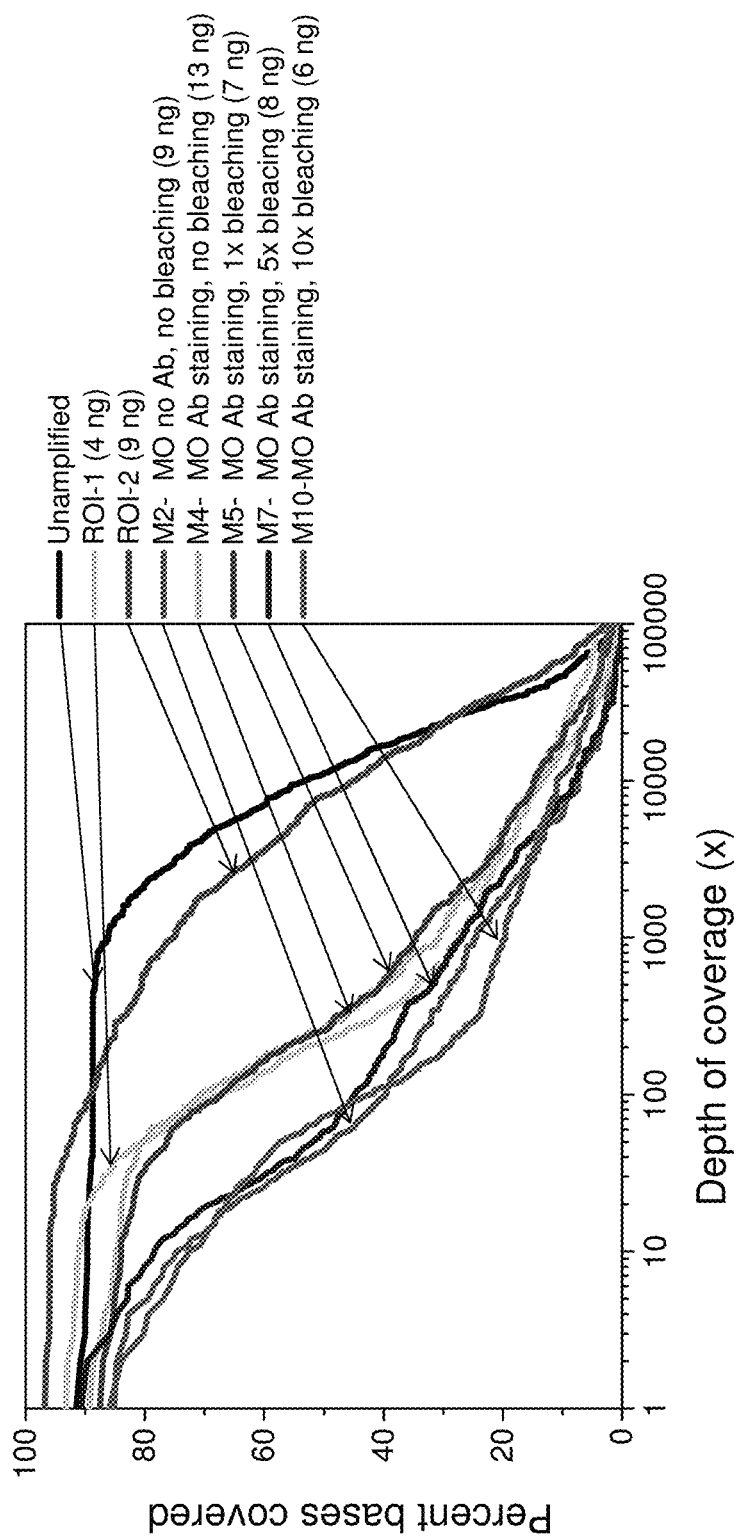
FIG. 8 shows sequencing data for DNA from FFPE samples subjected to up to 10 bleaching rounds.

This example was carried out in order to check the effect of repeated bleaching cycles on the quality of DNA in subsamples retrieved. Five sections of a SKVO3 ovarian carcinoma cell xenograft were mounted on microscope slides and treated as in Example 1. The immunofluorescence staining was performed with Cy3-labeled anti-PCK26 and Cy5-labeled anti-NaKATPase antibodies. Slide 1 was not stained at all, slide 2 stained one round without bleaching, slide 3 stained and bleached one round, slide 4 stained and bleached 5 rounds and slide 5 stained and bleached 10 rounds. 1.5 mm subsamples were retrieved from each slide and the DNA in the subsamples was amplified by rolling circle amplification and sequenced with ion semiconductor sequencing. As shown in FIG. 8, no major effect of the number of bleaching rounds was observed.

Example 4

This was an example to check the influence of the two bleaching reagents triphenyl monobenzyl borate and hydrogen peroxide on DNA. In one experiment, 5 microliters of 220 ng/microliter gDNA was subjected to the two bleaching reagents and in a second experiment 8 microliters of 128 ng/microliter DNA extracted from FFPE SKVO3 ovarian carcinoma cell xenograft was subjected to the same reagents.

a) Triphenyl Monobenzyl Borate

The sample was incubated in an aqueous solution of 1 mM triphenyl monobenzyl borate and 0.1 mM 1,4-diazabicyclo(2,2,2)octane (DABCO) under irradiation with >500 nm light for 7 min. The DNA was precipitated with Sure-Clean.

b) Hydrogen Peroxide

The sample was incubated in a freshly made aqueous solution of 3% H2O2 and 0.1 M NaHCO3. The DNA was precipitated with SureClean.

After incubation, the DNA was subjected to qPCR (HBB, 218 bp) and the results, as shown by Table 2, indicated that the incubation did not have any effect on the DNA quality.

| Sample | $C_T$ |
|---|---|
| gDNA control | 25 |
| gDNA triphenyl monobenzyl borate | 25 |
| gDNA hydrogen peroxide | 25 |
| FFPE control | 28 |
| FFPE triphenyl monobenzyl borate | 28 |
| FFPE hydrogen peroxide | 28 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

What is claimed is:

1. A method for determining a nucleotide sequence of a nucleic acid segment present in a biological sample, comprising the steps of:
    a) generating one or more first fluorescent images of said sample by a protocol comprising immunofluorescence detection of at least five different target proteins in said sample by repeated cycles of i) immunofluorescence staining, ii) capture of an immunofluorescent image, and iii) bleaching of the sample, and generating a plurality of second fluorescent images of said sample by the repeated cycles of i)-iii);
    b) selecting a region of interest of said sample by comparing said one or more first fluorescent images and second fluorescent images to a pattern of expression levels for the different proteins, wherein the pattern is qualitative, semiquantitative, or quantitative;
    c) removing a subsample from said region of interest, and;
    d) determining a nucleotide sequence of a nucleic acid segment present in said subsample,
    wherein each of the plurality of second fluorescent images are generated by a protocol comprising immunofluorescence detection of at least one of the at least five target proteins in said sample and fluorescence detection of at least one morphological feature in said sample, and
    wherein each of the plurality of second fluorescent images separately capture each of the at least five different target proteins.

2. The method of claim 1, wherein in step a) said one or more first images comprise a composite image obtained by overlaying a plurality of immunofluorescent images of said sample.

3. The method of claim 1, wherein said immunofluorescence staining comprises contacting the sample with an antibody against one of the at least five different target proteins, conjugated with a fluorophore.

4. The method of claim 3, wherein said fluorophore is a cyanine dye comprising Cy3 or Cy5.

5. The method of claim 1, wherein said bleaching comprises contacting said sample with a peroxide or an organic borate.

6. The method of claim 1, wherein the sample is further stained with a fluorescent marker that provides morphological information.

7. The method of claim 6, wherein signals from said fluorescent marker are used to provide location information for the overlaying of said immunofluorescent images.

8. The method of claim 6, wherein said fluorescent marker is a nucleus stain comprising 4',6-diamidino-2-phenylindole.

9. The method claim 1, wherein said at least five different target proteins comprise at least one of EGFR, HER2, HER3, cMET, PI3K, phosphorylated AKT, S6, phospho ERK1/2, PCK26, AE1 and NaKATPase.

10. The method of claim 1, wherein step a) further comprises fluorescence in situ hybridization staining of said sample followed by capture of a fluorescent hybridization image and overlaying of said fluorescent hybridization image with said plurality of immunofluorescent images.

11. The method of claim 10, wherein said fluorescence in situ hybridization staining comprises contacting the sample with an oligonucleotide capable of hybridizing with a target nucleic acid region in said sample, conjugated with a fluorophore.

12. The method of claim 11, wherein said target nucleic acid region is cMYC or CEP8.

13. The method of claim 1, wherein said biological sample is affixed to a solid support.

14. The method of claim 13, wherein said solid support is a microscope slide having a positively charged surface.

15. The method of claim 13, further comprising detecting an autofluorescence intensity of the solid support, wherein said solid support has the autofluorescence intensity of less than 1% of an average immunofluorescence intensity over a region of interest in said sample.

16. The method of claim 1, wherein in step c) said subsample is removed using laser microdissection or micromilling.

17. The method of claim 1, wherein a circle-equivalent diameter of said subsample is less than 2 mm.

18. The method of claim 1, wherein in step d) said nucleotide sequence is determined using ion semiconductor sequencing or Illumina dye sequencing.

19. The method of claim 1, wherein in step d) said nucleotide sequence is determined directly from said subsample.

20. The method of claim 1, wherein step d) is preceded by amplification of said nucleic acid segment.

21. The method of claim 1, wherein said biological sample is a tissue section.

* * * * *